United States Patent [19]

Reiffenrath et al.

[11] Patent Number: 5,356,560

[45] Date of Patent: Oct. 18, 1994

[54] 2-FLUOROPERFLUOROALKYLCYCLOHEXENE DERIVATIVES

[75] Inventors: Volker Reiffenrath, Rossdorf; Herbert Plach, Darmstadt, both of Fed. Rep. of Germany

[73] Assignee: Merck Patent Gesellschaft Mit Beschrankter Haftung, Darmstadt, Fed. Rep. of Germany

[21] Appl. No.: 109,568

[22] Filed: Aug. 20, 1993

[30] Foreign Application Priority Data

Aug. 23, 1992 [DE] Fed. Rep. of Germany ....... 4227772

[51] Int. Cl.$^5$ .................. C09K 19/52; C07C 23/10; C07C 43/20; C07D 213/62
[52] U.S. Cl. .................. 252/299.61; 252/299.62; 252/299.63; 252/299.64; 252/299.66; 544/335; 546/303; 549/369; 568/663; 568/669; 570/123; 570/186
[58] Field of Search ............ 252/299.61, 299.62, 252/299.63, 299.64, 299.65, 299.66; 544/298, 335; 546/303; 570/123, 186; 568/663, 669; 549/369; 359/103

[56] References Cited

U.S. PATENT DOCUMENTS 5,171,469 12/1992 Hittch et al. ............... 252/299.01

*Primary Examiner*—Shean Wu
*Attorney, Agent, or Firm*—Millen, White, Zelano, & Branigan

[57] ABSTRACT

2-Fluoroperfluoroalkylcyclohexene derivatives of the formula I

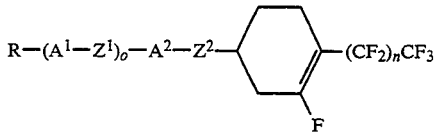

where
R is an alkyl or alkenyl radical having up to 18 carbon atoms which is unsubstituted or substituted by CN or by at least one halogen and in which one or more non-adjacent CH$_2$ groups may be replaced by a radical selected from the group consisting of —O—, —S—, —CO—, —O—CO—, —CO—O— and —C≡C—, A$^1$ and A$^2$ are each, independently of one another,
a) a 1,4-phenylene radical, in which one or two CH groups may be replaced by N,
b) a 1,4-cyclohexylene radical, in which one or two non-adjacent CH$_2$ groups may be replaced by —O— or —S—,
c) a 1,4-cyclohexenylene, piperidine-1,4-diyl, 1,4-bicyclo[2.2.2]octylene or naphthalene-2,6-diyl radical, where the radicals a) and b) may be monosubstituted or polysubstituted by halogen atoms, cyano groups and/or methyl groups, Z$^1$ and Z$^2$ are each, independently of one another, —CO—O—, —O—CO—, —CH$_2$CH$_2$—, —C≡C—, —CH=CH—, —OCH$_2$—, —CH$_2$O— or a single bond, or one of the radicals Z$^1$ and Z$^2$ is alternatively —(CH$_2$)$_4$— or —CH=CH—CH$_2$CH$_2$—, o is 0, 1 or 2, and
n is 0-7.

The derivatives of the present invention can be used as components of liquid-crystalline media for electro-optical display elements, in particular for matrix liquid-crystal displays.

12 Claims, No Drawings

2-FLUOROPERFLUOROALKYLCYCLOHEXENE DERIVATIVES

SUMMARY OF THE INVENTION

The present invention relates to 2-fluoroperfluoroalkylcyclohexene derivatives of the formula I

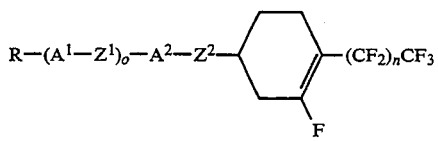

I where

R is an alkyl or alkenyl radical having up to 18 carbon atoms which is unsubstituted or substituted by CN or by at least one halogen and in which one or more non-adjacent $CH_2$ groups may be replaced by a radical selected from the group consisting of —O—, —S—, —CO—, —O—CO—, —CO—O— and —C≡C—, $A^1$ and $A^2$ are each, independently of one another, a) a 1,4-phenylene radical, in which one or two CH groups may be replaced by N, b) a 1,4-cyclohexylene radical, in which one or two non-adjacent $CH_2$ groups may be replaced by —O— or —S—, c) a 1,4-cyclohexenylene, piperidine-1,4-diyl, 1,4-bicyclo[2.2.2]octylene or naphthalene-2,6-diyl radical, where the radicals a) and b) may be monosubstituted or polysubstituted by halogen atoms, cyano groups and/or methyl groups, $Z^1$ and $Z^2$ are each, independently of one another, —CO—O—, —O—CO—, —$CH_2CH_2$—, —CH=CH—, —$OCH_2$—, —$CH_2O$—, —C≡C— or a single bond, or one of the radicals $Z^1$ and $Z^2$ is alternatively —$(CH_2)_4$— or —CH=CH—$CH_2CH_2$—, o is 0, 1 or 2, and n is 0–7.

The invention furthermore relates to the use of these compounds as components of liquid-crystalline media, and to liquid-crystal and electro-optical display elements which contain the liquid-crystalline media according to the invention.

DETAILED DESCRIPTION OF THE PREFERRED EMBODIMENTS

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering, in particular for matrix liquid-crystal displays (MLC displays).

The invention had the object of finding novel, stable, liquid-crystalline or mesogenic compounds which are suitable as components of liquid-crystalline media and have, in particular, relatively low viscosity and moderate positive dielectric anisotropy.

It has now been found that compounds of the formula I are eminently suitable as components of liquid-crystalline phases. In particular, they have relatively low viscosities. They can be used to obtain stable liquid-crystalline phases having a broad mesophase range, advantageous values for the optical and dielectric anisotropy and simultaneously very favourable values for the specific resistance. This allows considerable advantages to be achieved, in particular in the case of media for matrix liquid-crystal displays (MLC displays) or supertwist displays.

Similar compounds having liquid-crystalline properties, but containing no lateral fluorine, are mentioned, for example, in DE 39 11 621.

In addition, the provision of the compounds of the formula I very generally considerably broadens the range of liquid-crystalline substances which are suitable from various applicational points of view for the preparation of liquid-crystalline mixtures.

The compounds of the formula I have a broad range of applications. Depending on the choice of substituents, these compounds can be used as base materials from which liquid-crystalline phases are predominantly composed; however, it is also possible to add compounds of the formula I to liquid-crystalline base materials from other classes of compound, in order, for example, to modify the dielectric and/or optical anisotropy of a dielectric of this type and/or to optimise its threshold voltage and/or its viscosity and/or its specific resistance.

In the pure state, the compounds of the formula I are colourless and form liquid-crystalline mesophases in a temperature range which is favourably located for electro-optical use. They are stable chemically, thermally and to light.

The invention thus relates to the compounds of the formula I, in particular the compounds of the formula I in which n=0 and/or in which the radicals $A^1$ and $A^2$ are each, independently of one another, a cyclohexylene radical, in which one or two non-adjacent $CH_2$ groups may be replaced by —O— or —S—.

The invention furthermore relates to the use of these compounds as components of liquid-crystalline media.

The invention furthermore relates to liquid-crystalline media containing at least one compound of the formula I, and to liquid-crystal display elements, in particular electro-optical display elements, in particular matrix liquid-crystal displays which contain media of this type.

For reasons of simplicity below, $A^3$ denotes

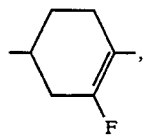

X denotes —$(CF_2)_nCF_3$, Cyc denotes a 1,4-cyclohexylene or 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo[2.2.2]octylene radical, where Cyc and/or Phe may be unsubstituted or monosubstituted or disubstituted by F or CN.

Accordingly, the compounds of the formula I include bicyclic compounds of the sub-formulae Ia and Ib:

R—$A^2$—$A^3$—X          Ia

| | |
|---|---|
| A—A²—Z²—A³—X | Ib | tricyclic compounds of the sub-formulae Ic to If:

| | |
|---|---|
| R—A¹—A²—A³—X | Ic |
| R—A¹—Z¹—A²—A³—X | Id |
| R—A¹—A²—Z²—A³—X | Ie |
| R—A¹—Z¹—A²—Z²—A³—X | If | and tetracyclic compounds of the subformulae Ig to In:

| | |
|---|---|
| R—A¹—A¹—A²—A³—X | Ig |
| R—A¹—Z¹—A¹—A²—A³—X | Ih |
| R—A¹—A¹—Z¹—A²—A³—X | Ii |
| R—A¹—A¹—A²—Z²—A³—X | Ij |
| R—A¹—Z¹—A¹—Z¹—A²—A³—X | Ik |
| R—A¹—Z¹—A¹—A²—Z²—A³—X | Il |
| R—A¹—A¹—Z¹—A²—Z²—A³—X | Im |
| R—A¹—Z¹—A¹—Z¹—A²—Z²—A³—X | In |

Of these, those of the sub-formulae Ia, Ib, Ic, Id, Ie and Ig are particularly preferred.

The preferred compounds of the sub-formula Ia include those of the sub-formulae Iaa to Iae:

| | |
|---|---|
| R—Phe—A³—X | Iaa |
| R—Cyc—A³—X | Iab |
| R—Dio—A³—X | Iac |
| R—Pyr—A³—X | Iad |
| R—Pyd—A³—X | Iae |

Of these, those of the formulae Iaa and Iab are particularly preferred.

The preferred compounds of the sub-formula Ib include those of the sub-formulae Iba to Ibl:

| | |
|---|---|
| R—Phe—CH₂CH₂—A³—X | Iba |
| R—Cyc—CH₂CH₂—A³—X | Ibb |
| R—Cyc—CH₂O—A³—X | Ibc |
| R—Phe—CH₂O—A³—X | Ibd |
| R—Phe—CO—O—A³—X | Ibe |
| R—Cyc—CO—O—A³—X | Ibf |
| R—Cyc—C≡C—A³—X | Ibg |
| R—Phe—C≡C—A³—X | Ibh |
| R—Phe—OCH₂—A³—X | Ibi |
| R—Cyc—OCH₂—A³—X | Ibj |
| R—Cyc—O—CO—A³—X | Ibk |
| R—Phe—O—CO—A³—X | Ibl |

The preferred compounds of the sub-formula Ic include those of the sub-formulae Ica to Ich:

| | |
|---|---|
| R—Cyc—Cyc—A³—X | Ica |
| R—Phe—Cyc—A³—X | Icb |
| R—Phe—Phe—A³—X | Icc |
| R—Cyc—Phe—A³—X | Icd |
| R—Pyd—Phe—A³—X | Ice |
| R—Pyd—Cyc—A³—X | Icf |
| R—Pyr—Cyc—A³—X | Icg |
| R—Pyr—Phe—A³—X | Ich |

Of these, those of the formulae Ica, Icb and Icc are particularly preferred.

The preferred compounds of the sub-formula Id include those of the sub-formulae Ida to Idi:

| | |
|---|---|
| R—Phe—Z¹—Phe—A³—X | Ida |
| R—Phe—Z¹—Cyc—A³—X | Idb |
| R—Cyc—Z¹—Cyc—A³—X | Idc |
| R—Pyr—Z¹—Cyc—A³—X | Idd |
| R—Pyd—Z¹—Cyc—A³—X | Ide |
| R—Pyd—Z¹—Phe—A³—X | Idf |
| R—Pyr—Z¹—Phe—A³—X | Idg |
| R—Cyc—Z¹—Dio—A³—X | Idh |
| R—Phe—Z¹—Dio—A³—X | Idi |

The preferred compounds of the sub-formula Ie include those of the sub-formulae Iea to Iei:

| | |
|---|---|
| R—Phe—Phe—Z²—A³—X | Iea |
| R—Phe—Cyc—Z²—A³—X | Ieb |
| R—Cyc—Cyc—Z²—A³—X | Iec |
| R—Cyc—Phe—Z²—A³—X | Ied |
| R—Pyr—Phe—Z²—A³—X | Iee |
| R—Pyd—Phe—Z²—A³—X | Ief |
| R—Phe—Pyr—Z²—A³—X | Ieg |
| R—Phe—Pyd—Z²—A³—X | Ieh |
| R—Phe—Dio—Z²—A³—X | Iei |

The preferred compounds of the sub-formula If include those of the sub-formulae Ifa to Ifg:

| | |
|---|---|
| R—Phe—Z¹—Phe—Z²—A³—X | Ifa |
| R—Phe—Z¹—Cyc—Z²—A³—X | Ifb |
| R—Cyc—Z¹—Cyc—Z²—A³—X | Ifc |
| R—Cyc—Z¹—Phe—Z²—A³—X | Ifd |
| R—Cyc—Z¹—Bi—Z²—A³—X | Ife |
| R—Cyc—Z¹—Dio—Z²—A³—X | Iff |
| R—Dio—Z¹—Cyc—Z²—A³—X | Ifg |

In the compounds of the formulae above and below, X is preferably a trifluoromethyl group (n=0).

Particularly preferred compounds are the cyclohexene derivatives of the formula I1 to I8.

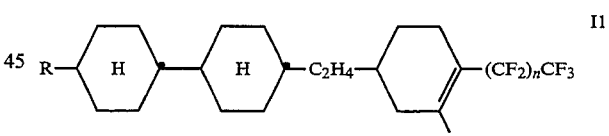

I1

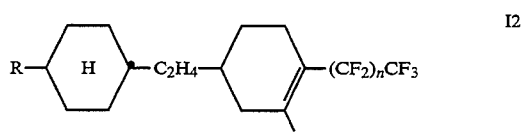

I2

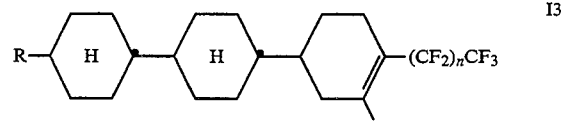

I3

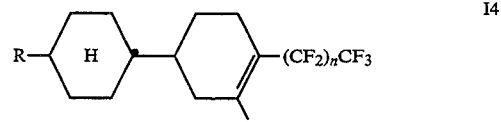

I4

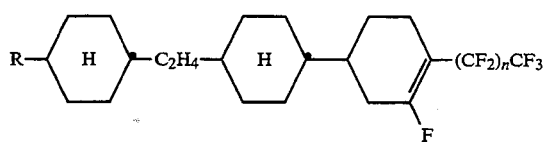

I5

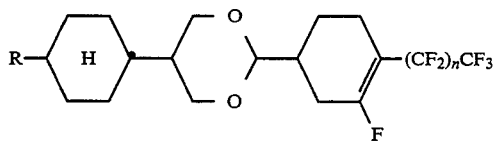

I6

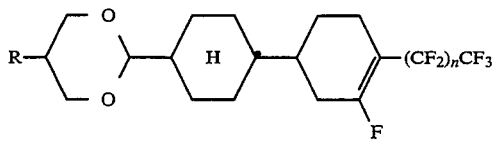

I7

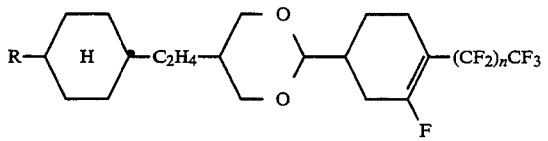

I8

Particularly preferred compounds are those of the formula IA and IB:

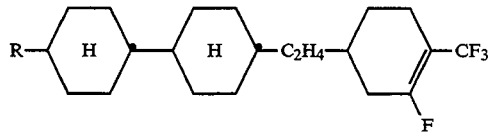

IA

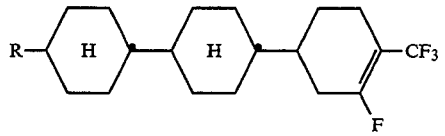

IB

In the compounds of the formula I which contain one or more bridges $Z^1$ and/or $Z^2$, these bridging men%bets are preferably —CO—O—, —O—CO— or —CH$_2$CH$_2$—, and secondarily preferably —CH$_2$O— or —OCH$_2$—.

R is preferably alkyl, furthermore alkoxy, F, Cl or CN. $A^1$ and/or $A^2$ are preferably Phe, Cyc, Che, Pyr or Dio. The compounds of the formula I preferably contain not more than one of the radicals Bi, Pyd, Pyr, Dio and Dit.

Preference is also given to compounds of the formula I and of all the sub-formulae in which $A^1$ and/or $A^2$ is 1,4-phenylene which is monosubstituted or disubstituted by F or monosubstituted by CN. In particular, these are 2-fluoro-1,4-phenylene, 3-fluoro-1,4-phenylene and 2,3-difluoro-1,4-phenylene, and 2-cyano-1,4-phenylene or 3-cyano-1,4-phenylene.

If R is an alkyl radical or an alkoxy radical, this may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 5-, 6-, 7- or 8-oxanonyl, or 2-, 3-, 4-, 5-, 6-, 7-, 8- or 9-oxadecyl.

If R is an alkenyl radical, this may be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl or dec-1-, -2-, -3-, -4-, -5-, -6-, -7-, -8- or -9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxylmethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If R is an alkenyl radical in which one CH$_2$ group has been replaced by CO or CO—O or O—CO—, this may be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R which are suitable for polymerisation reactions are suitable for the preparation of liquid-crystalline polymers.

Compounds of the formula I containing branched wing groups R may occasionally be of importance due to better solubility in the customary liquid-crystalline base materials, but in particular as chiral dopes if they are optically active. Smectic compounds of this type are suitable as components of ferroelectric materials.

Compounds of the formula I having $S_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctanoyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl- 3-oxapentyl and 2-methyl-3-oxahexyl.

If R is an alkyl radical in which two or more CH$_2$ groups have been replaced by —O— and/or —CO—O—, this may be straight-chain or branched. It is preferably branched and has 3 to 12 carbon atoms. Accordingly, it is in particular biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bismethoxycarbonyl)ethyl, 3,3-bis(methoxycarbonyl)propyl, 4,4-bis-(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(-methoxycarbonyl)octyl, his(ethoxycarbonyl)methyl, 2,2-bis(ethoxycarbonyl)ethyl, 3,3-bis-(ethoxycarbonyl)-propyl, 4,4-bis(ethoxycarbonyl)-butyl or 5,5-bis(ethoxycarbonyl)hexyl.

Compounds of the formula I which contain wing groups R which are suitable for polycondensation reactions are suitable for the preparation of liquid-crystalline polycondensates.

The formula I covers the racemates of these compounds and the optical antipodes, and mixtures thereof.

Of these compounds of the formula I and of the subformulae, those are preferred in which at least one of the radicals present therein has one of the preferred meanings indicated.

In the compounds of the formula I, preferred stereoisomers are those in which the rings Cyc and piperidine are trans-1,4-disubstituted. Those of the abovementioned formulae which contain one or more groups Pyd, Pyr and/or Dio in each case include the two 2,5-positional isomers.

The 1,4-cyclohexenylene group preferably has the following structures:

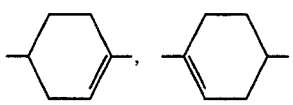

The compounds of the formula I are prepared by methods known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and are suitable for said reactions. Use may also be made here of variants which are known per se, but are not mentioned in greater detail.

The 2-fluorotrifluoromethylcyclohexene derivatives (n=0) of the formula I according to the invention can be prepared, for example, as follows:

Scheme 1

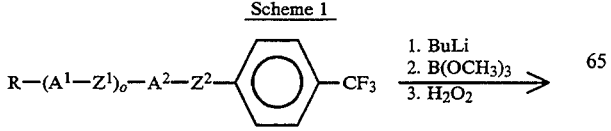

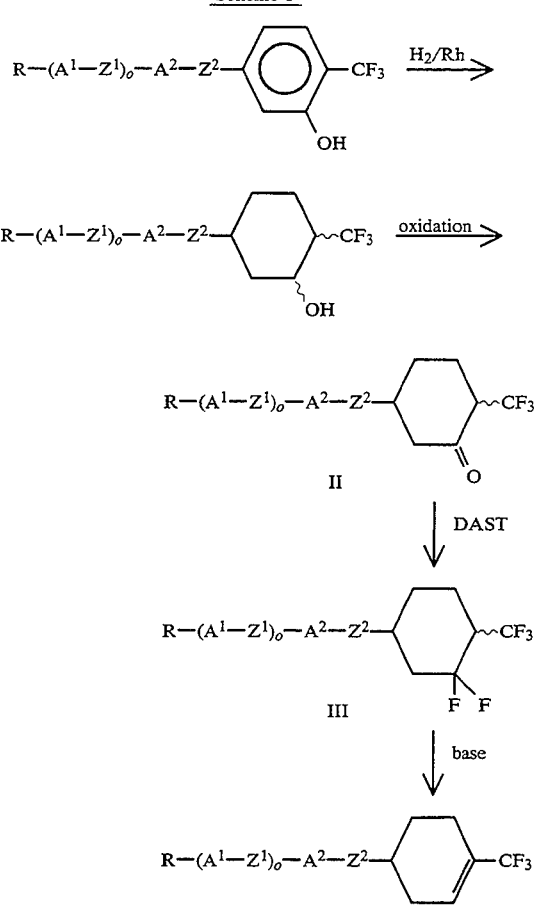

Suitable dehydrating agents for the compounds of the formula II or III are, for example, P$_2$O$_5$, POCl$_3$, PCl$_3$, PCl$_5$, COCl$_2$ and diethylaminosulfur trifluoride (DAST).

The synthesis of some particularly preferred compounds is indicated in greater detail below:

Scheme 2

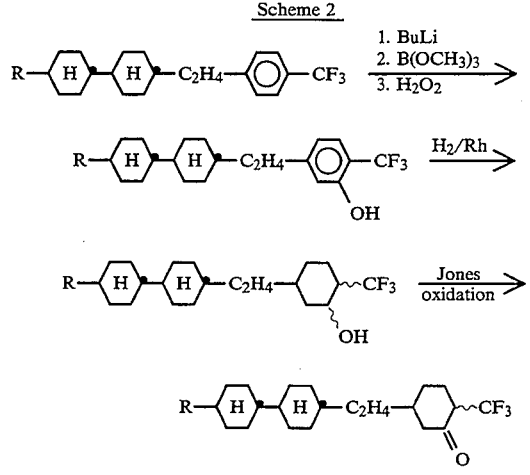

-continued
Scheme 2

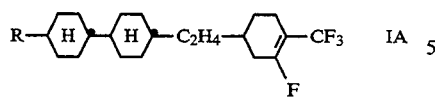

-continued
Scheme 3

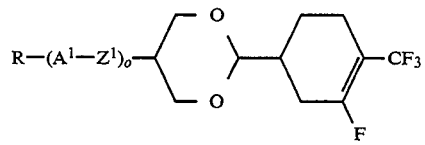

The compounds of the formulae II, III and IA are novel and are thus likewise the subject-matter of the invention.

In addition, the compounds of the formula I can also be prepared by reacting the corresponding 4-substituted 1-trifluoromethylcyclohexenes of the formula IIA

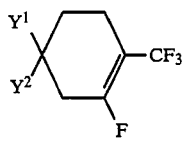

in which
$Y^1$ is —$(CH_2)_n$—$Y^3$, —CHO or CN,
$y^2$ is H,
$y^3$ is OH, halogen or O—$SO_2$—$C_3H_7$ and
n is 0, 1 or 2,
with the appropriately substituted compounds of the formula IIB

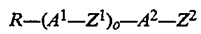

The compounds of the formula I in which $Z^2$ is $CH_2O$ or $OCH_2$ are obtained, for example, by etherification of the compounds of the formula IIA in which $Y^1$ is $(CH_2)_n$—$Y^3$ by means of the compounds of the formula IIB in which $Z^2$ is $CH_2OH$ or OH.

The compounds of the formula I in which $Z^2$ is $CH_2CH_2$ can be prepared, for example, by reacting the compounds of the formula IIB in which $Z^2$ is $CH_2$Met and Met is Li, Na, K, P*$(C_6H_5)_3$ or $P(O)(OC_2H_5)_2$ with the compounds of the formula IIA in which $Y^1$ is CN or CHO, and by subsequent reduction of the resultant ketone or ethylene derivative.

The compounds of the formula I in which $Z^2$ is a single bond can be prepared, for example, by reacting the compounds of the formula IIB in which $Z^2$ is Met with the compounds of the formula IIA in which $Y^1$ and $Y^2$ together are O, subsequently dehydrating the products and, if desired, catalytically hydrogenating the resultant cyclohexene derivative.

2-(4-Trifluoromethylcyclohexyl)dioxanes of the formula I4 are prepared in accordance with Scheme 3 by condensation of appropriately substituted propanediols with 4-formyltrifluoromethylcyclohexene derivatives.

Scheme 3

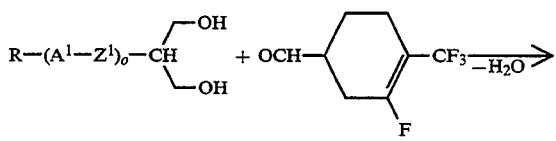

If desired, the starting materials can also be formed in situ by not isolating them from the reaction mixture, but instead immediately converting them further into the compounds of the formula I. The starting materials are all known and are described in, for example, DE 39 28 783.

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes; phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —$CF_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention preferably also contain components from the group comprising the compounds 1b, 2b, 3b, 4b and 5b (Group 2), whose proportions are preferably as follows:
Group 1: 20 to 90%, in particular 30 to 90%,
Group 2: 10 to 80%, in particular 10 to 50%,
the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

In particular, the media according to the invention are suitable for use in MLC displays.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited herein, and of corresponding German Application P 42 27 772.8, are hereby incorporated by reference.

EXAMPLES

The examples below are intended to illustrate the invention without representing a limitation. m.p.=melting point, c.p.=clearing point. Above and below, percentages are per cent by weight; all temperatures are indicated in degrees Celsius. "Customary work-up" means that water is added, the mixture is extracted with dichloromethane, and the organic phase is separated off, dried and evaporated, and the product is purified by crystallisation and/or chromatography.

In addition, the abbreviations have the following meanings:
C: crystalline-solid state, S: smectic phase (the index characterises the phase type), N: nematic state, Ch: cholesteric phase, I: isotropic phase. The number between two symbols indicates the conversion temperature in degrees Celsius.

| DAST | diethylaminosulfur trifluoride |
|---|---|
| DCC | dicyclohexylcarbodiimide |
| DDQ | dichlorodicyanobenzoquinone |
| DIBALH | diisobutylaluminium hydride |
| DMSO | dimethyl sulfoxide |
| POT | potassium tertiary-butanolate |
| THF | tetrahydrofuran |
| pTsOH | p-toluenesulfonic acid |

Example 1

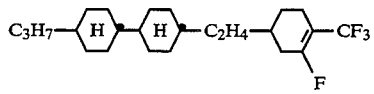

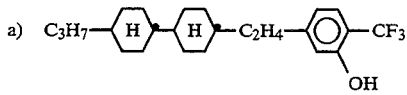

0.25 mol of n-butyllithium is added dropwise at room temperature to 0.25 mol of 1-[trans-4-(trans-4-propylcyclohexyl)-cyclohexyl]-2-(p-trifluoromethylphenyl)ethane and 0.25 mol of TMEDA in 1,000 ml of hexane. The reaction mixture is subsequently stirred at 40° C. for 2 hours and cooled to 0° C., and 0.25 mol of trimethyl borate is added dropwise. The mixture is stirred at 0°-3° C. for 0.5 hour, and 0.75 mol of glacial acetic acid is added. The reaction mixture is stirred overnight, and subsequently water and methyl tert-butyl ether are added. Finally, the product is subjected to customary work-up.

b) 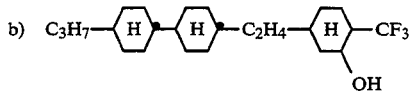

0.13 mol of 1-[trans-4-(trans-4-propylcyclohexyl)cyclohexyl]-2-(p-trifluoromethyl-2-hydroxy)phenyl)ethane, dissolved in 500 ml of ethanol, is hydrogenated at 5 bar and 60° C. with 8 of rhodium on charcoal. The catalyst is filtered off, and the solution is evaporated.

c) 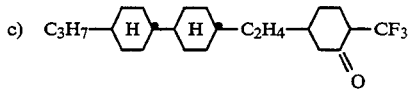

The product from Example 1b) (0.136 mol) is dissolved in 600 ml of acetone and 15 ml of isopropanol, and 0.136 mol of Jones reagent (2.67 mol/l) is added dropwise with stirring. The temperature should not exceed 25° C. The mixture is then stirred at this temperature for a further 2 hours. The organic layer is separated off and subjected to customary work-up.

d) 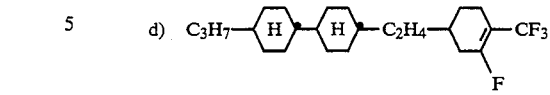

The 2-trifluoromethylcyclohexanone derivative (67.4 mmol) is dissolved in 150 ml of dichloromethane and 0.135 mol of DAST is added. The reaction mixture is stirred overnight and then poured into water. The product is subsequently subjected to customary work-up. C 69 $S_s$ 95N 116.7 I, $\Delta\epsilon=9.01$; $\Delta n=0.052$.

The following compounds of the formula

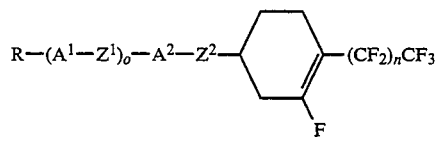

are prepared analogously:

| R | $-(A^1-Z^1)_o-A^2-Z^2-$ | n |
|---|---|---|
| n-$C_3H_7$ | phenyl | 0 |
| n-$C_3H_7$ | phenyl | 1 |
| n-$C_5H_{11}$ | phenyl | 0 |
| n-$C_5H_{11}$ | phenyl | 2 |
| n-$C_6H_{13}$ | phenyl | 0 |
| n-$C_6H_{13}$ | phenyl | 3 |
| $CH_3O$ | phenyl | 0 |
| $CH_3O$ | phenyl | 1 |

-continued

| R | $-(A^1-Z^1)_o-A^2-Z^2-$ | n |
|---|---|---|
| n-C$_3$H$_7$ | phenyl-phenyl | 0 |
| n-C$_3$H$_7$ | phenyl-phenyl | 1 |
| n-C$_5$H$_{11}$ | phenyl-phenyl | 0 |
| n-C$_5$H$_{11}$ | phenyl-phenyl | 1 |
| n-C$_6$H$_{13}$ | phenyl-phenyl | 0 |
| n-C$_6$H$_{13}$ | phenyl-phenyl | 2 |
| C$_2$H$_5$ | Cy-Cy-C$_2$H$_4$- | 0 |
| C$_2$H$_5$ | Cy-Cy-C$_2$H$_4$- | 1 |
| n-C$_5$H$_{11}$ | Cy-Cy-C$_2$H$_4$- | 0 C 59 S$_B$ 109 N 116.9 I, Δε = 10.28 Δn = +0.061 |
| n-C$_6$H$_{13}$ | Cy-Cy-C$_2$H$_4$- | 0 |
| n-C$_6$H$_{13}$ | Cy-Cy-C$_2$H$_4$- | 1 |
| CH$_3$CH$_2$OCH$_2$ | Cy-C$_2$H$_4$- | 0 |
| CH$_3$CH$_2$OCH$_2$ | Cy-C$_2$H$_4$- | 2 |

-continued
| R | $-(A^1-Z^1)_o-A^2-Z^2-$ | n |
|---|---|---|
| n-$C_5H_{11}$ | 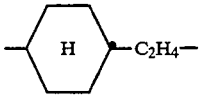 | 0 |
| n-$C_5H_{11}$ | 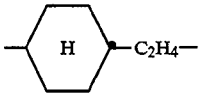 | 1 |
| n-$C_6H_{13}$ | 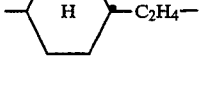 | 0 |
| n-$C_6H_{13}$ | 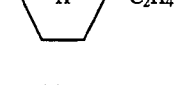 | 1 |
| n-$C_3H_7$ | 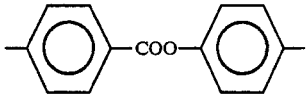 | 0 |
| n-$C_3H_7$ | 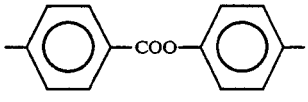 | 1 |
| n-$C_5H_{11}$ | 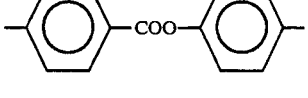 | 0 |
| n-$C_5H_{11}$ |  | 2 |
| n-$C_3H_7$ | 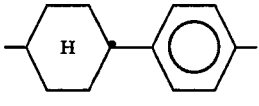 | 0 |
| n-$C_3H_7$ | 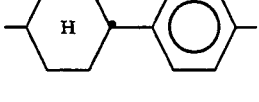 | 1 |
| n-$C_5H_{11}$ |  | 0 |
| n-$C_5H_{11}$ |  | 1 |
| n-$C_3H_7$ | 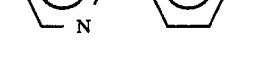 | 0 |

-continued
| R | $-(A^1-Z^1)_o-A^2-Z^2-$ | n |
|---|---|---|
| n-C$_3$H$_7$ | 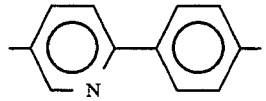 | 2 |
| n-C$_5$H$_{11}$ | 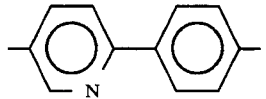 | 0 |
| n-C$_5$H$_{11}$ | 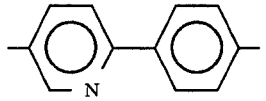 | 3 |
| n-C$_3$H$_7$ | 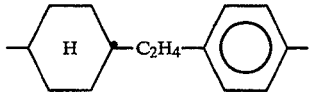 | 0 |
| n-C$_3$H$_7$ | 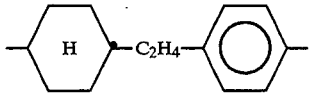 | 2 |
| n-C$_5$H$_{11}$ | 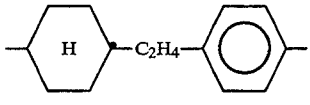 | 0 |
| n-C$_5$H$_{11}$ | 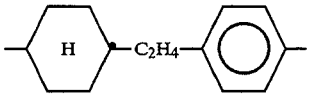 | 3 |
| n-C$_3$H$_7$ | 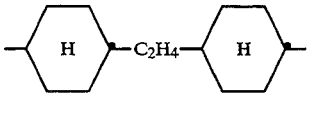 | 0 |
| n-C$_3$H$_7$ | 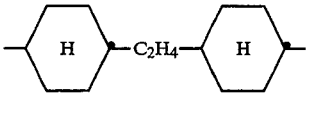 | 1 |
| n-C$_4$H$_9$ | 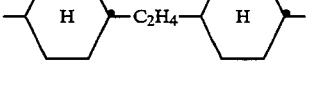 | 0 |
| n-C$_4$H$_9$ | 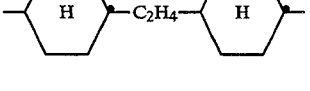 | 1 |
| n-C$_5$H$_{11}$ | 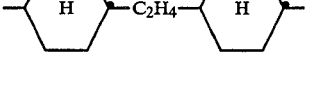 | 0 |
| n-C$_5$H$_{11}$ | 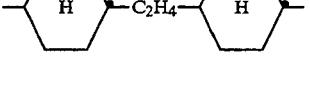 | 1 |

| R | $-(A^1-Z^1)_o-A^2-Z^2-$ | n |
|---|---|---|
| n-C$_6$H$_{13}$ | cyclohexyl-C$_2$H$_4$-cyclohexyl | 0 |
| n-C$_6$H$_{13}$ | cyclohexyl-C$_2$H$_4$-cyclohexyl | 2 |
| n-C$_3$H$_7$ | dioxane-phenyl | 0 |
| n-C$_3$H$_7$ | dioxane-phenyl | 1 |
| n-C$_5$H$_{11}$ | dioxane-phenyl | 0 |
| n-C$_5$H$_{11}$ | dioxane-phenyl | 1 |
| n-C$_3$H$_7$ | pyrimidine-phenyl | 0 |
| n-C$_3$H$_7$ | pyrimidine-phenyl | 2 |
| n-C$_5$H$_{11}$ | pyrimidine-phenyl | 0 |
| n-C$_5$H$_{11}$ | pyrimidine-phenyl | 1 |

Example 2

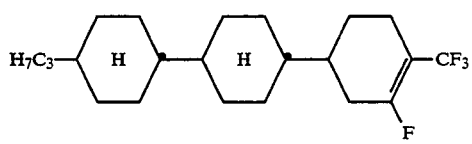

a)

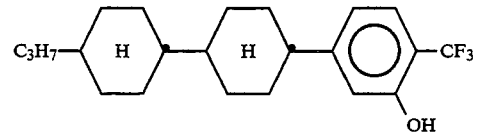

Analogously to Example 1a), 0.25 mol of TMEDA in 1,000 ml of hexane and 0.25 mol of BuLi are added dropwise to 0.25 mol of p-[trans-4-(trans-4-propylcyclohexyl)cyclohexyl]trifluoromethylbenzene. The mixture is stirred at 40° C. for 2 hours and cooled to 0° C., and 0.25 mol of trimethyl borate is added. The mixture is stirred at 0°–3° C. for a further 0.5 hour, 0.75 mol of glacial acetic acid is added, and the reaction mixture is stirred overnight. After addition of methyl tert-butyl ether, the product is subjected to customary work-up.

b) 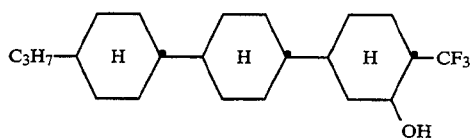

0.13 mol of p-[trans-4-(trans-4-propylcyclohexyl)cyclohexyl]-1-trifluoromethyl-2-hydroxybenzene is dissolved in 500 ml of ethanol and hydrogenated at 5 bar and 60° C. with 8 g of rhodium on charcoal.

c) 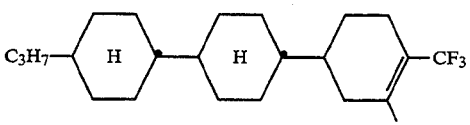

The reaction of the hydroxyl compound with Jones reagent and DAST is carried out analogously to Example 1c) and 1d).
C 116N 129.2 I; Δε=10.43, Δn=+0.063.
The following compounds of the formula

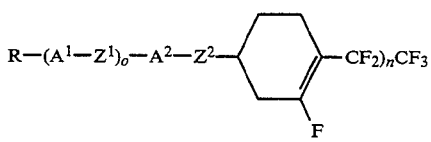

are obtained analogously:

| R | $-(A^1-Z^1)_o-A^2-Z^2-$ | n |
|---|---|---|
| C₂H₅ |  | 0 |
| C₂H₅ | 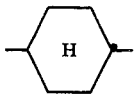 | 1 |
| n-C₃H₇ | 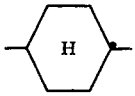 | 0 |
| n-C₃H₇ |  | 2 |
| n-C₅H₁₁ | 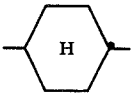 | 0 |

-continued

| R | $-(A^1-Z^1)_o-A^2-Z^2-$ | n |
|---|---|---|
| n-C₅H₁₁ | (H) | 1 |
| n-C₆H₁₃ | (H) | 0 |
| n-C₆H₁₃ | (H) | 1 |
| CH₃ | (H)-(H) | 0 |
| CH₃ | (H)-(H) | 1 |
| C₂H₅ | (H)-(H) | 0 |
| C₂H₅ | (H)-(H) | 1 |
| n-C₄H₉ | (H)-(H) | 0 |
| n-C₄H₉ | (H)-(H) | 2 |
| n-C₅H₁₁ | (H)-(H) | 0 |
| n-C₅H₁₁ | (H)-(H) | 1 |
| n-C₆H₁₃ | (H)-(H) | 0 |
| n-C₆H₁₃ | (H)-(H) | 2 |

| R | $-(A^1-Z^1)_o-A^2-Z^2-$ | n |
|---|---|---|
| C₂H₅ | cyclohexyl-dioxolane | 0 |
| C₂H₅ | cyclohexyl-dioxolane | 1 |
| n-C₃H₇ | cyclohexyl-dioxolane | 0 |
| n-C₃H₇ | cyclohexyl-dioxolane | 1 |
| C₅H₁₁ | cyclohexyl-dioxolane | 0 |
| C₅H₁₁ | cyclohexyl-dioxolane | 2 |
| C₂H₅ | dioxolane-cyclohexyl | 0 |
| C₂H₅ | dioxolane-cyclohexyl | 2 |
| n-C₃H₇ | dioxolane-cyclohexyl | 0 |
| n-C₃H₇ | dioxolane-cyclohexyl | 1 |
| n-C₅H₁₁ | dioxolane-cyclohexyl | 0 |
| n-C₅H₁₁ | dioxolane-cyclohexyl | 2 |
| C₂H₅ | cyclohexyl-C₂H₄-dioxolane | 0 |
| C₂H₅ | cyclohexyl-C₂H₄-dioxolane | 1 |
| n-C₃H₇ | cyclohexyl-C₂H₄-dioxolane | 0 |
| n-C₃H₇ | cyclohexyl-C₂H₄-dioxolane | 2 |
| n-C₄H₉ | cyclohexyl-C₂H₄-dioxolane | 0 |
| n-C₄H₉ | cyclohexyl-C₂H₄-dioxolane | 1 |
| n-C₅H₁₁ | cyclohexyl-C₂H₄-dioxolane | 0 |
| n-C₅H₁₁ | cyclohexyl-C₂H₄-dioxolane | 2 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. 2-Fluoroperfluoroalkylcyclohexene derivatives of the formula I

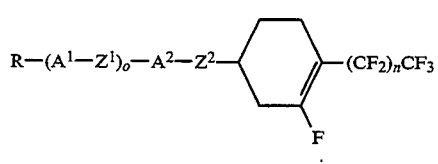

where

R is an alkyl or alkenyl radical having up to 18 carbon atoms which is unsubstituted or substituted by CN or by at least one halogen and in which one or more non-adjacent CH₂ groups can be replaced by a radical selected from the group consisting of —O—, —S—, —CO—, —O—CO—, —CO—O— and —O—, A¹ and A² are each, independently of one another, a) a 1,4-phenylene radical, in which one or two CH groups can be replaced by N,
b) a 1,4-cyclohexylene radical, in which one or two non-adjacent CH$_2$ groups can be replaced by —O— or —S—,
c) a 1,4-cyclohexenylene, piperidine-1,4-diyl, 1,4-bicyclooctylene or naphthalene-2,6-diyl radical, where the radicals a) and b) can be monosubstituted or polysubstituted by halogen atoms, cyano groups and/or methyl groups, Z$^1$ and Z$^2$ are each, independently of one another, —CO—O—, —O—CO—, —CH$_2$CH$_2$—, —C≡C—, —CH=CH—, —OCH$_2$—, —CH$_2$O— or a single bond, or one of the radicals Z$^1$ and Z$^2$ is alternatively —(CH$_2$)$_4$— or —CH=CH—CH$_2$CH$_2$—, o is 0, 1 or 2, and n is 0–7.

2. 2-Fluorotrifluoromethylcyclohexene derivatives according to claim 1, characterized in that n=0.

3. 2-Fluoroperfluoroalkylcyclohexene derivatives according to claim 1, characterised in that A$^1$ and A$^2$ are 1,4-cyclohexylene radicals, in which one or two non-adjacent CH$_2$ groups can be replaced by —O— or —S—.

4. 2-Fluoroperfluoroalkylcyclohexene derivatives according to claim 1, wherein Z$^2$ is —O—CO— or —CH$_2$CH$_2$—.

5. Trifluoromethylcyclohexanone derivatives of the formula II

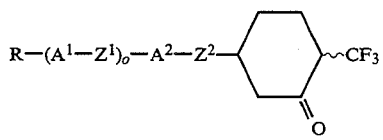

II in which

R is an alkyl or alkenyl radical having up to 18 carbon atoms which is unsubstituted or substituted by CN or by at least one halogen and in which one or more non-adjacent CH$_2$ groups can be replaced by a radical selected from the group consisting of —O—, —S—, —CO—, —O—CO—, —CO—O— and —C≡C—, A$^1$ and A$^2$ are each, independently of one another,
a) a 1,4-phenylene radical, in which one or two CH groups can be replaced by N,
b) a 1,4-cyclohexylene radical, in which one or two non-adjacent CH$_2$ groups may be replaced by —O— or —S—,
c) a 1,4-cyclohexenylene, piperidine-1,4-diyl, 1,4-bicyclo octylene or naphthalene-2,6-diyl radical, where the radicals a) and b) can be monosubstituted or polysubstituted by halogen atoms, cyano groups and/or methyl groups, Z$^1$ and Z$^2$ are each, independently of one another, —CO—, —O—CO—, —CH$_2$CH$_2$—, —C≡C—, —CH=CH—, —OCH$_2$—, —CH$_2$O— or a single bond, or one of the radicals Z$^1$ and Z$^2$ is alternatively —(CH$_2$)$_4$— or —CH=CH—CH$_2$CH$_2$—, and o is 0, 1 or 2.

6. 2,2-Difluorotrifluoromethylcyclohexane derivatives of the formula III

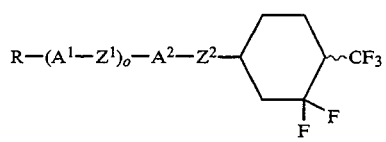

III in which

R is an alkyl or alkenyl radical having up to 18 carbon atoms which is unsubstituted or substituted by CN or by at least one halogen and in which one or more non-adjacent CH$_2$ groups can be replaced by a radical selected from the group consisting of —O—, —S—, —CO—, —O—CO—, —CO—O— and —C≡C—, A$^1$ and A$^2$ are each, independently of one another,
a) a 1,4-phenylene radical, in which one or two CH groups can be replaced by N,
b) a 1,4-cyclohexylene radical, in which one or two non-adjacent CH$_2$ groups may be replaced by —O— or —S—,
c) a 1,4-cyclohexenylene, piperidine-1,4-diyl, 1,4-bicyclooctylene or naphthalene-2,6-divl radical, where the radicals a) and b) can be monosubstituted or polysubstituted by halogen atoms, cyano groups and/or methyl groups, Z$^1$ and Z$^2$ are each, independently of one another, —CO—O—, —O—CO—, —CH$_2$CH$_2$—, —C≡C—, —C=Ch—, —OCH$_2$—, —CH$_2$O— or a single bond, or one of the radicals Z$^1$ and Z$^2$ is alternatively —(CH$_2$)$_4$— or —CH=CH—CH$_2$CH$_2$—, and o is 0, 1 or 2.

7. 2-Fluorotrifluoromethylcyclohexene derivatives of the formula IA

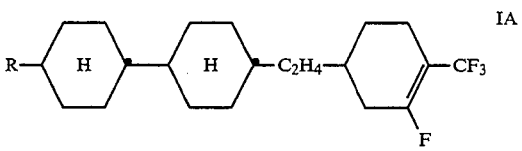

IA in which R is as defined in claim 1.

8. 2-Fluorotrifluoromethylcyclohexene derivatives of the formula IB

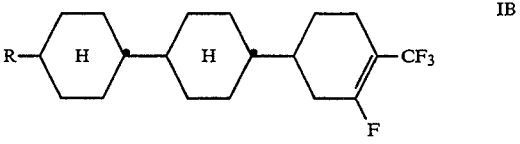

IB in which R is as defined in claim 1.

9. A method which comprises incorporating one or compounds of formula I of claim 1 as a component of liquid-crystalline media for an electro-optical display element.

10. Liquid-crystalline medium having at least two components, wherein one or more components are a compound of formula I of claim 1.

11. Electro-optical display element, which comprises, as dielectric, a liquid-crystalline medium according to claim 10.

12. Matrix liquid-crystal display element, which comprises, as dielectric, a liquid-crystalline medium according to claim 10.

* * * * *